US009783829B2

United States Patent
Hendry et al.

(10) Patent No.: US 9,783,829 B2
(45) Date of Patent: *Oct. 10, 2017

(54) PROCESS FOR ENHANCING BIOGENIC METHANE PRODUCTION FROM A CARBONACEOUS MATERIAL USING GASEOUS NITROGEN COMBINATIONS

(71) Applicant: COMMONWEALTH SCIENTIFIC AND INDUSTRIAL RESEARCH ORGANISATION, Australian Capital Territory (AU)

(72) Inventors: Philip Hendry, Leichhardt (AU); David Midgley, Berowa (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,957

(22) PCT Filed: Dec. 19, 2013

(86) PCT No.: PCT/AU2013/001486
§ 371 (c)(1),
(2) Date: Jun. 17, 2015

(87) PCT Pub. No.: WO2014/094053
PCT Pub. Date: Jun. 26, 2014

(65) Prior Publication Data
US 2015/0329876 A1    Nov. 19, 2015

(30) Foreign Application Priority Data

Dec. 19, 2012  (AU) ................................ 2012905563
Jul. 30, 2013   (AU) ................................ 2013902824

(51) Int. Cl.
| | |
|---|---|
| C09K 8/582 | (2006.01) |
| C12P 5/02  | (2006.01) |
| C12N 1/38  | (2006.01) |
| C12M 1/00  | (2006.01) |
| C12M 1/107 | (2006.01) |
| C09K 8/62  | (2006.01) |

(52) U.S. Cl.
CPC .............. *C12P 5/023* (2013.01); *C09K 8/582* (2013.01); *C09K 8/62* (2013.01); *C12M 21/04* (2013.01); *C12M 29/00* (2013.01); *C12M 47/00* (2013.01); *C12N 1/38* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 6,143,534 A | * | 11/2000 | Menger | C12M 21/04 210/603 |
| 8,051,908 B2 | * | 11/2011 | Pfeiffer | E21B 43/40 166/246 |
| 2006/0223154 A1 | * | 10/2006 | Kohr | C12M 21/04 435/166 |
| 2011/0250582 A1 | * | 10/2011 | Gates | C09K 8/582 435/3 |
| 2011/0308790 A1 | * | 12/2011 | Strapoc | C09K 8/582 166/250.01 |
| 2012/0064609 A1 | * | 3/2012 | Clement | C10G 1/00 435/262 |
| 2012/0115201 A1 | * | 5/2012 | Adams | C10L 1/02 435/167 |
| 2015/0329765 A1 | * | 11/2015 | Hendry | C09K 8/582 435/167 |
| 2016/0319643 A1 | * | 11/2016 | Lambourne | C09K 8/582 |

FOREIGN PATENT DOCUMENTS

CN          102517368 A  *  6/2012

OTHER PUBLICATIONS

Shimizu S. et al. Geobiology Molecular Characterization of Microbial Comunities in Deep Coal Seam Groundwater of Northern Japan. vol. 5, pp. 423-433, 2007.*
Nazina T. et al. Regulation of Geochemical Activity of Microorganisms in a Petroleum Reservoir by Injection of Peroxide or Water-Air Mixture. Microbiology 77(3)324-333, 2008.*
Davies, et al. (2000), Efficient Improvement of Silage Additives by Using Genetic Algorithms; Applied and Environmental Microbiology, 66(4), 1435-1443.
Heylen, et al. (2006), Cultivation of Denitrifying Bacteria: Optimization of Isolation Conditions and Diversity Study; Applied and Environmental Microbiology, 72(4), 2637-2643.
Shimizu, et al. (2007)"Molecular Characterization of Microbial Communities in Deep Coal Seam Groundwater of Northern Japan." Geobiology 5.4, 423-33.

(Continued)

*Primary Examiner* — Ralph Gitomer
(74) *Attorney, Agent, or Firm* — Leason Ellis LLP (57) ABSTRACT

A nutrient combination for enhancing biogenic methane production from a carbonaceous material is described. The nutrient combination comprises a source of phosphorus (P) and gaseous nitrogen ($N_2$). The nutrient combination is preferably substantially fee of gaseous oxygen and/or gaseous $NO_x$ and/or $SO_x$. In various embodiments the nutrient combination may comprise a two-phase mixture of a solution of the soluble source of phosphorus (P) and gaseous nitrogen ($N_2$). A process for enhancing biogenic methane production from a carbonaceous material is also described. The process involves dispersing the nutrient combination of the invention throughout the carbonaceous material for a period of time to biogenically produce methane and subsequently collecting methane from the carbonaceous material.

18 Claims, 2 Drawing Sheets

(56) References Cited

OTHER PUBLICATIONS

Ferry J.G. (1993) Methanogenesis: Ecology, Physiology, Biochemistry & Genetics, Chapman and Hall, New York, 473-89.
DSMZ:Cultivation of Methanogens, URL: https://web.archive.org/web/20121031173456/http://www.dsmz/fileadmin/Bereiche/Microbiology/Dateien/Kultivierungshinweise/emgIMethanogene.pdf.
International Search Report and Written Opinion of PCT/AU13/01486.
Foundation and Development of Microbial Oil Recovery, Peng Yusheng, 2005, First Edition, p. 241, Petroleum Industry Press.

* cited by examiner

PROCESS FOR ENHANCING BIOGENIC METHANE PRODUCTION FROM A CARBONACEOUS MATERIAL USING GASEOUS NITROGEN COMBINATIONS

FIELD

The present invention relates to a nutrient combination, process and system for enhancing biogenic methane production from a carbonaceous material.

BACKGROUND

Methane is associated in varying amounts with most coal deposits. It may be formed thermogenically during burial and maturation of the coal or it may be produced biogenically by the action of microbes. Bacteria are considered to be the primary degraders of coal, producing a range of intermediates which are successively degraded to methane precursers such as hydrogen gas, carbon dioxide, acetate and various others compounds (e.g. dimethyl sulfide, formate, methanol and methylamines). These precursers are then converted to methane via methanogenic archaea. This methanogenic process may occur via a number of mechanisms including $CO_2$ reduction, acetoclastic (from acetate) or methylotrophic processes.

The coal seam environment in which biogenic methane is produced is anoxic and reducing. Due to macronutrient limitation biogenic methane production is slow and occurs over long time-scales. Production from a typical coal seam methane (CSM) well may occur for 5-7 years, after which time the rate of production becomes uneconomic and the well may be abandoned.

It may be possible to prolong the production life of the well by introducing methanogenic microbial populations. US Publication No. 2004/0033557 describes introducing a consortium of selected anaerobic microorganisms into a subsurface formation for in situ conversion of organic compounds in the formation into methane and other compounds.

It may also be possible to relatively rapidly replenish the methane within a buried coal seam by stimulation of the microbes that reside in the coal and/or associated water. It is known that this can be achieved by addition of nutrients to the system. For example, U.S. Pat. No. 7,832,475 describes a method for enhancement of biogenic methane production that involves introducing an indiscriminate microbial population stimulation combination, such as corn syrup, emulsified oil, and milk, to blanket boost microbial populations in a hydrocarbon-bearing formation. The method further involves subsequent manipulation of the microbial populations by selectively starving one or more microbial populations to selectively sustain at least one of the boosted microbial populations.

Whilst significant progress has been made in increasing methane production through enhancing growth in consortia of microbes, there is still further scope for improvement.

SUMMARY

According to a first aspect, there is provided a nutrient combination for enhancing biogenic methane production from a carbonaceous material comprising a source of phosphorus (P) and gaseous nitrogen ($N_2$).

For the purposes of the present description, the term "gaseous nitrogen" refers to nitrogen which is gaseous at atmospheric pressure and 25° C. As such, gaseous nitrogen may include gaseous nitrogen dissolved in an aqueous solution under pressures at or above atmospheric pressure.

The term 'carbonaceous material' is broadly used to refer to any carbon-containing substance capable of supporting, and are preferably present or provided with, one or more methanogenic microbial populations. The carbonaceous material may be subject to degradation by said one or more methanogenic microbial populations to produce methane or methane precursors. Suitable examples of carbonaceous material include, but are not limited to, coal, lignite, peat, drill cuttings, waste coal, coal derivatives, oil shale, oil formations, tar sands, hydrocarbon-contaminated soil and petroleum sludges. The carbonaceous material preferably comprises at least 0.5 wt % N and more preferably at least 1.0 wt % N on a dry ash-free basis.

The carbonaceous material may be in-situ carbonaceous material or ex-situ carbonaceous material. In-situ carbonaceous material may refer to carbonaceous material residing in an original source location such as a subterranean formation or goaf bearing carbonaceous material. Ex-situ may refer to a carbonaceous material that has been removed from its original source location. Ex-situ carbonaceous material may exist in a reactor, a bioreactor, a heaped pile or alternative above ground structures, a pit, and so forth.

In various embodiments the nutrient combination may comprise a two-phase mixture of a solution of the soluble source of phosphorus (P) and gaseous nitrogen ($N_2$). The solution may be an aqueous solution.

In some of these embodiments gaseous nitrogen ($N_2$) may also be soluble in the solution, such that a substantial portion (i.e. at least 20%, preferably at least 50% and most preferably at least 80%) of the gaseous nitrogen is dissolved in the solution at pressures at which it is delivered to the carbonaceous material. The concentration of nitrogen (N) dissolved in solution may be between 5 mg to 1750 mg, preferably between 10 mg and 1500 mg, more preferably between 50 mg and 1000 mg and even more preferably between 100 mg and 800 mg of gaseous nitrogen per kilogram of solvent, in particular water. The higher limit of the dissolved gaseous nitrogen will be limited by the solubility of nitrogen at the pressure at which the nutrient combination is delivered to or proximal to the carbonaceous source.

The gaseous nitrogen ($N_2$) preferably represents the substantial proportion (e.g. preferably greater than 60% v/v, more preferably greater than 95% v/v even more preferably greater than 99.5% v/v of the total gaseous component of the nutrient combination). The gaseous component is preferably a consistent composition (i.e. gaseous component preferably has a nitrogen content which fluctuates no more than 5% v/v and more preferably no more than 1% v/v over the delivery span of the nutrient combination) to ensure the microbial population does not suffer from detrimental fluctuations in their nutrient source. To this extent, the use of flue gases as a nitrogen gas ($N_2$) should preferably not be used, unless the flue gas has been processed to remove impurities, including residual oxygen and gaseous oxides of sulphur and nitrogen.

The nutrient combination may further comprise a non-gaseous source of nitrogen. Preferably, the non-gaseous source of nitrogen represents no more than 50 wt % and more preferably no more than 20 wt % of the total nitrogen source in the nutrient combination.

The nutrient combination may comprise a phosphorus concentration of at least 1.5 mM, preferably at least 2 mM and more preferably at least 5 mM.

Preferably, the nutrient combination further comprises one or more methanogenic microbial populations. More preferably the one or more methanogenic microbial populations comprises microbes selected from the group consisting of Methanobacteria, Methanococci, Methanomicrobia, Methanopyri.

According to a second aspect, there is provided a process for enhancing biogenic methane production from a carbonaceous material comprising the steps of:

dispersing a nutrient combination comprising a source of phosphorus (P) and gaseous nitrogen ($N_2$), or as otherwise defined above, throughout the carbonaceous material for a period of time to biogenically produce methane; and, collecting methane from the carbonaceous material.

Preferably, the nutrient combination is in intimate contact with the carbonaceous material to enable the nutrient combination to be readily available to the methanogenic microbial populations inhabited therein.

It will be understood by those skilled in the art that the dispersal of the nutrient combination throughout a carbonaceous material would not be achieved through the industrial scale gaseous blanketing of a carbonaceous material. Such processes do not enable the nutrient combination to penetrate and occupy the voids between particles of the carbonaceous material to enable the nutrient combination to be readily available to the methanogenic microbial populations.

Preferably, the dispersal of the carbonaceous material through the carbonaceous material is achieved through a mixing or agitating of the nutrient combination throughout existing environment proximate to the carbonaceous material (e.g. formation water).

The dispersal of the nutrient combination throughout the carbonaceous material may be achieved through adjusting the injection pressure of the nutrient combination into the carbonaceous material through known techniques available to those skilled in the relevant art.

In a preferred embodiment, the dispersal of the nutrient combination is achieved through sub-surface flow manipulation techniques, such as those disclosed in WO2011/017771, which is incorporated herein by reference.

Preferably, the period of time is at least one week, more preferably at least 2 weeks, even more preferably at least 3 months, yet even more preferably at least 6 months and most preferably at least one year. In general, the longer the time the nutrient combination is in intimate contact with the carbonaceous material, the greater the amount of methane will be produced for collection. Commercial consideration may at least partially drive the period of time at which the nutrient combination is dispersed throughout the carbonaceous material prior to the collection of methane from the carbonaceous material.

'Enhancing biogenic production of methane' may refer to increasing the volume of biogenic methane produced from the carbonaceous material in a given period relative to the volume of biogenic methane produced from the carbonaceous material in the absence of the nutrient combination in the same period. Alternatively, 'enhancing biogenic production of methane' may refer to accelerating the rate of production of biogenic methane from the carbonaceous material relative to the rate of production of biogenic methane produced from the carbonaceous material in the absence of the nutrient combination.

Enhancing biogenic production of methane may be achieved by increasing the size of the one or more methanogenic microbial populations or by increasing the rate of methanogenesis in said microbial populations.

The one or more methanogenic microbial populations may be any microbial population capable of methanogenesis, in other words which is capable of degrading the carbonaceous material to produce methane or methane precursors such as hydrogen gas, carbon dioxide, acetates and other organic compounds such as formates, methanol and methylamines.

Said microbial populations may be indigenous microbial populations which naturally occur or co-exist with the carbonaceous material.

Alternatively, or additionally, the methanogenic microbial populations may be introduced to the carbonaceous material. The introduced methanogenic microbial populations may be indigenous with respect to a separate or alternative carbonaceous material. Alternatively, the introduced methanogenic microbial populations may be from a bioreactor or engineered microbial cultures. Engineered microbial cultures include those produced through classical selection methods or other genetic modification methods.

According to a third aspect, there is provided a biogenic methane production system comprising:

a nutrient combination for enhancing biogenic methane from a carbonaceous material comprising a source of phosphorus (P) and gaseous nitrogen ($N_2$);

a delivery system for dispersing said nutrient combination throughout the carbonaceous material; and, a collector for collecting methane from the carbonaceous material.

According to a further aspect, there is provided an apparatus for enhancing biogenic methane production from a carbonaceous material, the apparatus comprising a delivery system capable of dispersing a nutrient combination comprising a source of phosphorus (P) and gaseous nitrogen ($N_2$) throughout the carbonaceous material.

According to a still further aspect, there is provided a use of gaseous nitrogen ($N_2$) in a nutrient combination comprising a source of phosphorus (P) and gaseous nitrogen ($N_2$) for enhancing biogenic production.

BRIEF DESCRIPTION OF THE FIGURES

Notwithstanding any other forms which may fall within the scope of the nutrient combination, process and system as set forth in the Summary, specific embodiments will now be described, by way of example only, with reference to the accompanying figures in which.

DETAILED DESCRIPTION

In one aspect, the present application relates to a nutrient combination for enhancing biogenic production of methane from a carbonaceous material.

Nutrient Combination

The nutrient combination for enhancing biogenic methane production from a carbonaceous material comprises a source of phosphorus (P) and gaseous nitrogen ($N_2$).

The nutrient combination is preferably substantially free of gaseous oxygen and/or gaseous $NO_x$ and/or $SO_x$. The presence of oxygen is detrimental to the preferred anaerobic microbial populations and the presence of $NO_x$ or $SO_x$ is likely to significantly change the pH and ionic strength of the nutrient combination which may inhibit rather than promote methane production by the microbial population.

In various embodiments the nutrient combination may comprise a two-phase mixture of a solution of the soluble source of phosphorus (P) and gaseous nitrogen ($N_2$).

The nutrient combination preferably further comprising a source of water. (i.e. the solution may be an aqueous solution).

The solvent (source of water) in the aqueous solution may be water, deionised water, ultrapure water, distilled water, municipal water, groundwater, produced water, formation water, recycled water, process water, wastewater, brackish water or brine.

Preferably, the aqueous solution comprises formation water or of a composition similar thereto. Through using an aqueous solution the same or similar to the formation water around the carbonaceous deposit, the amended (i.e. nutrient rich) aqueous solution is better able to deliver enhanced nutrients to the microbial population without a significant lag time to adapt to the new aqueous environment.

Preferably, the temperature, pH and/or ionic strength of the source of water is substantially the same as the temperature, pH and/or ionic strength of the resultant nutrient combination.

For the purposes of the present invention, substantially the same temperature is preferably a temperature difference of no more than 20° C., and more preferably 10° C.

For the purposes of the present invention, substantially the same pH is preferably a pH difference of no more than 2, more preferably no more than 1 and even more preferably no more than 0.5.

Preferably, the pH of the nutrient combination is in the pH range of 5.0 to 10.0, more preferably 6.0 to 9.0 and even more preferably 7.0 to 8.0.

For the purposes of the present invention, substantially the same ionic strength is preferably an ionic strength difference of no more than 100%, more preferably no more than 50% and even more preferably no more than 10%.

Preferably, the nutrient combination is substantially free of oxygen (i.e. anoxic).

In some embodiments, prior to formulation of the nutrient combination, the formation water (or other solvents) may be stored in a storage reservoir such as a storage tank or a dam. Accordingly, it will be appreciated that in these particular embodiments the formation water may need to first undergo treatment to remove oxygen therefrom. Such treatments may include, but is not limited to, purging the formation water (or other solvents) with a gas such as nitrogen or a similar inert gas to displace oxygen therein.

In some embodiments the concentration of phosphorus in the solution is at least 1.5 mM.

In some of these embodiments the gaseous nitrogen ($N_2$) may also be soluble in the solution. The concentration of nitrogen (N) in solution may be between 5 mg to 1750 mg of gaseous nitrogen per kilogram of solvent.

For embodiments in which the nutrient combination is a single phase, the pressure of the nutrient combination is preferably sufficiently high such that at least 5 mg and preferably at least 50 mg of gaseous nitrogen gas ($N_2$) is dissolved in the aqueous solution.

It will be appreciated that the source of phosphorus and the gaseous nitrogen may be selected to be soluble in the aqueous solution. It will also be appreciated that the solubility of the source of phosphorus may be enhanced in the aqueous solution with an emulsifying agent. Accordingly, the nutrient combination may further comprise an emulsifying agent.

In alternative embodiments the nutrient combination may comprise a two-phase mixture of an emulsion containing the soluble source of phosphorus (P) and gaseous nitrogen ($N_2$). The emulsion may be an oil-in-water emulsion. Alternatively, the nutrient combination may comprise a two-phase mixture of a colloid or a gel containing the soluble source of phosphorus (P) and gaseous nitrogen ($N_2$). Still further, the nutrient combination may comprise a two-phase mixture of a suspension containing the source of phosphorus (P) and the gaseous nitrogen ($N_2$).

In various embodiments the solution suspension, emulsion or gel of the nutrient combination may further comprise at least one trace element selected from the group comprising iron, manganese, cobalt, zinc, molybdenum, nickel, aluminium, boron, copper, tungsten and selenium. The trace element may be present in the solution as an aqueous soluble salt thereof. The concentration of each trace element in the nutrient combination may be less than 200 ppm.

In other embodiments the solution suspension, emulsion or gel of the nutrient combination may further comprise at least one vitamin selected from the group comprising pyridoxine, aminobenzoic acid, pantothenate, nicotinic acid, riboflavin, thiamine, thioctic acid, biotin, folic acid, pyruvate and B12. The concentration of each vitamin in the solution may be less than 100 ppm.

In further embodiments the solution, suspension, emulsion or gel of the nutrient combination may further comprise at least one stimulant. Stimulants may be any factors that can be used to increase or stimulate the biogenic production of methane in the carbonaceous material. Examples of stimulants include, but are not limited to, yeast extract, Coenzyme M, lactic acid, mineral amendments (such as chloride, sodium, potassium, magnesium and calcium), alkyl alcohols, methanol, ethanol, 2-propanol, 2,3 butanediol, vanillate, glycine, cysteine, 3,4,5-trimethoxybenzoate, cellulose, cinnamic acid, benzoic acid, chitin, chitosan, chlorate, perchlorate, and any combinations thereof.

Other additives may also be comprised in the solution in the nutrient combination for various purposes, for example to stabilise the solution against deterioration over time and prolong shelf life, maintain constant pH, and so forth. Such additives may include, but are not limited to, acids, bases, buffering agents, oxidants, anti-oxidants, surfactants, emulsifying agents, gelling agents, any combination thereof and the like.

Source of Phosphorus

The source of phosphorus in the nutrient combination may be any substance containing phosphorus in a form that is bioavailable to the one or more methanogenic microbial populations and has the effect of stimulating the biogenic production of methane. The method of determining whether a particular source of phosphorus has a stimulatory effect is well known to those skilled in the art.

In various embodiments, the source of phosphorus may be phosphorus containing compounds such as salts of phosphorus oxoacids, phospholipids or derivatives thereof, organophosphate esters, and any combination thereof and the like.

Examples of suitable salts of phosphorus oxoacids including, but not limited to, salts of hypophosphorus acid ($H_3PO_2$), phosphorus acid ($H_3PO_3$), metaphosphorus acid ($HPO_2$), orthophosphorus acid ($H_3PO_3$), metaphosphoric acids $((HPO_3)_n)$, polyphosphoric acids $((HPO_3)_{n+2})$, tripolyphosphoric acid $(H_5P_3O_{10})$, pyrophosphoric acid $(H_4P_2O_7)$, orthophosphoric acid $(H_3PO_4)$, and the like.

Examples of suitable phospholipids include, but are not limited to, lecithin wet gum, lecithin, cephalin, phosphatidate, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, and the like.

Examples of suitable phospholipid derivatives include, but are not limited to, natural phospholipid derivatives found in eggs, soy, hydrogenated soy, or synthetic phospholipd derivatives of phosphatidic acid, phosphatidylcholine, phosphatidylglycerol, phosphatidylethanolamine, phosphatidylserine, PEG phospholipids, and the like.

Examples of suitable organophosphate esters include, but are not limited to, trixylenyl phosphate ester, butylated phenol phosphate ester, isopropyl phenol phosphate ester, and the like.

Source of Nitrogen

The gaseous nitrogen $(N_2)$ is a gas at ambient temperature and pressure and is bioavailable to the one or more methanogenic microbial populations.

The gaseous nitrogen $(N_2)$ preferably represents the substantial proportion (e.g. preferably greater than 60% v/v, more preferably greater than 95% v/v even more preferably greater than 99.5% v/v of the total gaseous component of the nutrient combination).

In embodiments where the gaseous nitrogen is derived from spent combustion gases (i.e. flue gases), the spent combustion gases should undergo processing to ensure that the composition thereof is temporally consistent. Further, the processing should remove impurities therefrom, including residual oxygen and gaseous oxides.

It will be understood from the person skilled in the art that suitable sources of phosphorus or nitrogen may vary dependent upon the methanogenic microbial population and the carbonaceous material. The selection of suitable sources of phosphorous and nitrogen may be readily performed through a screening process in which the effectiveness of various nutrient combinations is tested upon specific carbonaceous material and methanogenic microbial populations.

Process for Enhancing Biogenic Methane Production

The nutrient combination described in the application may be employed in a process for enhancing biogenic methane production from a carbonaceous material.

The process comprises dispersing said nutrient combination throughout the carbonaceous material for a period of time to biogenically produce methane, and collecting methane from the carbonaceous material.

Dispersing the Nutrient Combination Throughout the Carbonaceous Material

It will be appreciated by persons skilled in the art that the manner for dispersing the nutrient combination throughout the carbonaceous material will depend on whether the carbonaceous material may be an in situ carbonaceous material or an ex situ carbonaceous material.

For example, dispersing the nutrient combination throughout an in situ carbonaceous material in the form of a subterranean formation bearing carbonaceous material (e.g. coal seam) may comprise injecting the nutrient combination into or proximal to naturally occurring or artificially induced fractures or cleat systems in the in situ carbonaceous material by injection techniques well understood by those skilled in the art of recovering CSM including, but not limited to, injection under pressure, by gravity forces, other water injection methods and the like.

Similarly, where the in situ carbonaceous material comprises an oil shale formation, dispersing the nutrient combination may comprise injecting the nutrient combination through the fractures of the oil shale formation. In another embodiment, dispersing the nutrient combination may comprise injecting the nutrient combination together with a hydraulic fracturing fluid, sand propant and various chemicals. In this way, the nutrient combination may be delivered to fractures in the carbonaceous material at the same time as the fractures are caused to form under high pressure from the hydraulic fracturing fluid and/or sand propant. In the latter embodiment, the use of hydraulic fracturing fluids under anoxic or suboxic conditions is preferred so that anoxic conditions in the fractures are maintained, or can be readily attained soon afterwards.

An alternative embodiment for dispersing the nutrient combination throughout the in situ carbonaceous material comprises providing one or more laterals to access the in situ carbonaceous material and injecting the nutrient combination into the laterals. Laterals may be provided roughly parallel (horizontal) to the tops and bottoms of in situ carbonaceous material. These laterals may be either drilled outwardly from a main well bore or may be generated through high-pressure water technology. High-pressure water jet technology may be suitably used to drill laterals through friable or more porous subsurface formations. Horizontally-drilled and/or water-jet laterals may extend hundreds or thousands of meters from the main well bore, and therefore, provide much better access to the carbonaceous material. Furthermore, particularly in porous subsurface formations, injected nutrient combination will tend to move through a permeable or porous subsurface formation under capillary action, thereby migrating into smaller fractures and microfractures in the carbonaceous material.

It will be appreciated that injecting the nutrient combination may be continuous or intermittent. Further, injecting the nutrient combination may cease entirely after an initial period, said period being sufficient to bring a sufficient volume of nutrient combination into intimate contact with the carbonaceous material.

In situ carbonaceous material may co-exist with associated water or formation water. In the case of fractured oil shale formations there may also be some hydraulic fracturing fluid associated with the carbonaceous material. The presence of these fluids in or proximal to the carbonaceous material may serve to dilute the solution in the nutrient combination. Accordingly, it will be appreciated that in some embodiments dispersing a nutrient combination may comprise delivering a concentrated solution comprised in the nutrient combination to the carbonaceous material, whereby the delivered concentrated solution undergoes dilution with fluids associated with the carbonaceous material to provide a solution in the nutrient combination having an effective phosphorus concentration of at least 1.5 mM. The concentrations of the source of phosphorus in the concentrated solution may be calculated according to the known or estimated degree of dilution.

With respect to ex situ carbonaceous material, the manner for dispersing the nutrient combination throughout the carbonaceous material may vary.

For example, in embodiments where the ex situ carbonaceous material may be arranged in a heaped pile, dispersing the nutrient combination throughout the heaped pile of carbonaceous material may comprise applying the solution of the nutrient combination, under an atmosphere of gaseous nitrogen, to an outer surface of the heaped pile in an amount sufficient to cause the solution to flow or trickle under gravity from the outer surface through underlying carbonaceous material in the heaped pile. In some embodiments the gaseous nitrogen source is applied to the heaped pile under positive pressure to ensure that the gaseous nitrogen penetrates and occupies any voids between the carbonaceous material in the heaped pile.

The amount of nutrient combination that may be applied to the heaped pile may be calculated by considering the height and volume of the heaped pile, particle size of the carbonaceous material, and like factors.

In other embodiments, where the ex situ carbonaceous material may be in a reactor (or bioreactor), dispersing the nutrient combination throughout the carbonaceous material may comprise mixing the nutrient combination with the carbonaceous material under an atmosphere of the gaseous nitrogen source. It will be appreciated that mixing may be continuous or intermittent. Further, mixing may cease entirely after an initial mixing period, said period being sufficient to bring the nutrient combination into intimate contact with the carbonaceous material.

Period of Time to Biogenically Produce Methane

The period of time to biogenically produce methane will vary according to several factors including, but not limited to, environmental conditions, the nature and size of the carbonaceous material, and the nature and size of the one or more microbial populations.

It will generally be understood that an incubation period may be required. The incubation period may extend from the time of delivering the nutrient combination to the carbonaceous material to the time at which biogenic methane production is increased relative to biogenic methane production in the absence of the nutrient combination. The one or more microbial populations may grow to a sufficient size to enhance biogenic methane production during the incubation period. The incubation period may extend around from weeks to years, although this may vary according to the aforementioned factors.

Collecting Methane

It will be appreciated by persons skilled in the art that the manner for collecting the methane will depend on whether the carbonaceous material may be an in situ carbonaceous material or an ex situ carbonaceous material.

In respect of in situ carbonaceous material, the techniques for collecting methane are well understood by those skilled in the art of recovering CSM and associated gas from various recovery wells of oil and gas bearing subterranean formations. For example, to extract the gas, a steel-encased hole may be drilled into the coal seam (100-1500 meters below ground). As the pressure within the coal seam declines due to natural production or the pumping of water from the coalbed, both gas and 'produced water' come to the surface through tubing. Then the gas is sent to a compressor station and into natural gas pipelines.

Similarly, in respect of ex situ carbonaceous material, the techniques for collecting methane are well understood by those skilled in the art of recovering biogas from reactors, bioreactors, heaped piles, and so forth. For example, the ex situ carbonaceous material may be confined in a closed space to retain the biogenic methane in a headspace thereof. The closed space may be defined by a shell disposed over the ex situ carbonaceous material, or any suitable covering such as a tarpaulin. The methane may be withdrawn from the headspace under positive or negative pressure.

System for Enhancing Biogenic Methane Production

The biogenic methane production system comprises:
the nutrient combination as described in the application;
a delivery system for dispersing said nutrient combination throughout the carbonaceous material; and,
a means for collecting methane from the carbonaceous material.

Delivery System for Dispersing said Nutrient Combination Throughout the Carbonaceous Material It will be appreciated by persons skilled in the art that the delivery system for dispersing the nutrient combination throughout the carbonaceous material will depend on whether the carbonaceous material may be an in situ carbonaceous material or an ex situ carbonaceous material.

Preferably the delivery system is an anoxic delivery system.

The delivery system for dispersing the nutrient combination throughout an in situ carbonaceous material may comprise an injection system for injecting the nutrient combination into or proximal to the in situ carbonaceous material. Such systems are well understood by those skilled in the art of recovering CSM and may include, but are not limited to, injection under pressure, by gravity forces, other water injection methods and the like. In some embodiments, such systems may be adapted to co-inject the nutrient combination with a further injection fluid, such as a hydraulic fracturing fluid.

With respect to ex situ carbonaceous material, the delivery system for dispersing the nutrient combination throughout the carbonaceous material may vary.

In some embodiments the delivery system for dispersing the nutrient combination throughout a heaped pile of carbonaceous material (or an above ground structure of carbonaceous material) may comprise an applicator for applying the nutrient combination to the outer surface of the heaped pile (or the above ground structure). Suitable applicators include, but are not limited to, a drip system disposed above the heaped pile or said structure.

The drip system may be operatively associated with a liquid volume controller, a plurality of sensors and so forth to control the amount of nutrient combination applied to the heaped pile or said structure. The liquid volume controller, sensors and so forth may be programmed to ensure that the nutrient combination is applied in a sufficient amount to cause it to flow or trickle under gravity from the outer surface of the heaped pile or said structure through the underlying carbonaceous material.

The heaped pile may also be confined in a closed space to maintain the heaped pile in an atmosphere of gaseous nitrogen. The closed space may be defined by a shell disposed over the heaped pile, or any suitable covering such as a tarpaulin. Said covering need not be substantially gas tight, particularly if gaseous nitrogen is supplied to the heaped pile under positive pressure. Gaseous nitrogen may be applied to the closed space through one or more input ports in the covering.

In other embodiments, the delivery system for dispersing the nutrient combination throughout the carbonaceous material in a reactor (or a bioreactor) comprises a conduit in fluid communication with the reactor (or bioreactor) for conveying the nutrient combination to the reactor, and a mixer. The mixer may be any suitable mixer capable of mixing a three phase mixture.

Collector for Collecting Methane

It will be appreciated by persons skilled in the art that the collector for collecting the methane will depend on whether the carbonaceous material may be an in situ carbonaceous material or an ex situ carbonaceous material.

In respect of in situ carbonaceous material, the collector for collecting methane are well understood by those skilled in the art of recovering CSM and associated gas from various oil and gas bearing subterranean formations. For example, recovery wells may be drilled to recover methane from the in situ carbonaceous material. The recovery well may be in fluid communication with a compressor to compress the recovered methane, and a storage reservoir or transport conduit for natural gas distribution. Similarly, in respect of ex situ carbonaceous material, various collectors for collecting methane are well understood by those skilled in the art of recovering biogas from reactors, bioreactors, heaped piles, and so forth. For example, the collector may comprise a shell disposed over the ex situ carbonaceous material, or any suitable covering such as a tarpaulin, to confine the biogenic methane in a headspace thereof.

The covering may be provided with one or more ports therein in fluid communication with a pump and reservoir configured to withdraw methane from the headspace under positive or negative pressure.

It will be appreciated that the geometry of injection sites, laterals and recovery wells can be variable, but must be based on local geologic, structural, and hydrologic conditions in order to maximise the injection volumes of nutrient combination (concentrate) and to attain maximum recovery of methane. Additionally, at some point in time, the carbonaceous material between the injection sites or laterals and the recovery wells may become methanogenically unproductive. Subsequently, the recovery wells may be converted into injection sites and a new series of recovery wells may be drilled.

Apparatus for Enhancing Biogenic Methane Production

The apparatus may carry out the process for enhancing biogenic methane production as described above.

The apparatus may comprise a delivery system capable of dispersing a nutrient combination comprising a source of phosphorus (P) and gaseous nitrogen ($N_2$) throughout the carbonaceous material. In particular the apparatus may comprise a delivery system capable of bringing a two phase mixture of the nutrient combination into intimate contact with the carbonaceous material.

In some embodiments, the delivery system may be capable of co-injecting the gaseous nitrogen ($N_2$) and the solution (or the emulsion, the suspension or the gel) of the source of phosphorus (P) into the in situ carbonaceous material. In other embodiments, the delivery system may be capable of separately injecting the gaseous nitrogen ($N_2$) and the solution (or the emulsion, the suspension or the gel) of the source of phosphorus (P) into the in situ carbonaceous material. In the latter embodiments, the delivery system may be adapted to inject the gaseous nitrogen ($N_2$) prior to, at the same time as, or after the solution (or the emulsion, the suspension or the gel) of the source of phosphorus (P).

It will be appreciated that the delivery system may be adapted to provide for dissolution of the gaseous nitrogen ($N_2$) into the solution (or the emulsion, the suspension or the gel) of the source of phosphorus (P) as the two phase mixture is subjected to increasing pressure at depth.

EXAMPLES

Non-limiting Examples of a nutrient combination and process for enhancing biogenic methane production will now be described.

Samples

Two microbial consortia were used in the experiments described in this manuscript. The first was MBC3/4, a methanogenic enrichment culture derived from a coal seam formation water sample obtained from a well in the Port Phillip Basin, Victoria, Australia. The sample was sourced from a borehole that intersected a brown coal-seam at approximately 90 m subsurface.

The second was obtained from a coal-seam formation water sample originating in the Surat Basin, Queensland, Australia. Two samples were obtained from that location, one large volume was collected in a plastic carboy, shipped to the lab, filter sterilised and used as medium. The second smaller sample was collected on site and immediately degassed by bubbling helium through it, followed by the addition of $Na_2S$ to retain the reducing conditions. After shipping to the lab, this was stored anoxically and used as the microbiological inoculum for experiments. The coals used as feedstock were a brown coal from Maddingley brown coal mine in Victoria, Australia and a mixed Surat Basin coal of sub-bituminous maturity, and from around 500 to 700 meters subsurface, supplied by Origin Australia.

Microcosm Cultures

Example 1

Using the MBC3/4 sample, triplicate cultures were established in modified MSY (mMSY) liquid medium (Li et al., 2008) that contained (per liter) 0.5 g yeast extract (Oxoid, Hampshire, UK); 0.4 g $K_2HPO_4.3H_2O$; 0.1 g $MgCl_2.6H_2O$; 1 ml of a 0.1% resazurin solution; 1 ml of SL-11 trace element solution (containing per liter: 10 ml 25% HCl; 1.5 g $FeCl_2.4H_2O$; 0.1 g $MnCl_2.4H_2O$; 0.19 g $CoCl_2.6H_2O$; 70 mg $ZnCl_2$; 36 mg $NaMoO_4.2H_2O$; 24 mg $NiCl_2.2H_2O$; 10 mg $AlKPO_4$; 6 mg $H_3BO_3$; 2 mg $CuCl_2.2H_2O$; 0.1 µg $Na_2SeO_3$) prior to autoclaving. For a nitrogen source, cultures were either supplied with 100 mg/l $NH_4Cl$ under a 95% nitrogen gas headspace, or with the 95% nitrogen gas headspace alone. After autoclaving, the hot medium was transferred to the anoxic glove box filled with a mixture of 95% $N_2$ and 5% $H_2$. After the medium had cooled to <50° C., 1 ml of a filter sterile vitamin solution (containing per liter: 10 mg pyridoxine HCl; 5 mg 4-aminobenzoic acid; 5 mg Ca pantothenate; 5 mg nicotinic acid; 5 mg riboflavin; 5 mg thiamine; 5 mg thioctic acid; 2 mg biotin; 2 mg folic acid and 0.1 mg B12), 1 ml of filter sterile 100 µM $Na_2S$ solution containing 0.1% resazurin and 0.5 ml of 1.3 M cysteine HCl solution were also added, and the solution allowed to equilibrate for ~2 hours (all chemicals were from Sigma, except for $K_2HPO_4.3H_2O$, $NH_4Cl$, $MgCl_2.6H_2O$ supplied by Nuplex, New Zealand). The final medium pH was 6.8. Fifty ml of mMSY medium was then transferred aseptically to triplicate sterile, 120 ml serum vials (Crown Scientific, New South Wales, Australia) and inoculated with 1 ml of the MBC3/4 sample. The flasks were then sealed with butyl-rubber septa and aluminium crimps (Grace Davison Discovery Sciences, Illinois, USA) and removed from the anoxic glove box. Cultures were inverted and incubated in the dark, shaking (50 RPM) at 30° C. Culture vials were incubated in an inverted position to minimise loss of gases through the butyl rubber septa. Methane was measured by weekly by GC as described. The headspace gas was replaced after each sample was taken.

Example 2

Using the Surat coal sample, cultures were established which included 20 ml of filter sterile, reduced coal-seam formation water along with a 2 ml volume of crushed Surat coal (<1.2 mm>0.5 mm) in 120 ml serum vials. The headspace gas mixture in these vials was initially ~100% helium. Four hundred mg of $K_2HPO_4.3H_2O$ per liter of fluid was added to triplicate vials as a source of phosphorus, additional nitrogen was either absent or delivered either in the form of $NH_4Cl$ (100 mg/l) or a headspace of ~100% nitrogen gas instead of helium. The vials were inoculated with 1 ml of an enrichment culture of the Surat basin water having been grown on coal for about 8 weeks. Vials were then sealed, removed from the anoxic glove box and incubated as described above at 42° C. Methane was measured by GC at 4 weeks of incubation.

Example 3

Using the Surat coal sample, cultures were established which included 20 ml of filter sterile, reduced coal-seam formation water along with a 2 ml volume of crushed Surat coal (<1.2 mm>0.5 mm) in 120 ml serum vials. The headspace gas mixture in these vials was initially ~100% helium. Four hundred mg of $K_2HPO_4.3H_2O$ per liter of fluid was added to triplicate vials as a source of phosphorus, additional nitrogen was either absent or delivered either in the form of $NH_4Cl$ (100 mg/l) or a headspace of ~100% nitrogen gas instead of helium. The vials were inoculated with 5 ml of an enrichment culture of the Surat basin water having been grown on coal for about 8 weeks. Vials were then sealed, removed from the anoxic glove box and incubated as described above at 42° C. Methane was measured by GC at 4 weeks of incubation.

Gas Measurement

Gas sampling was carried out inside the anoxic glove box for all samples. For the Maddingley brown coal and the MBC3/4 consortium (Example 1), five ml gas samples were collected from sealed flasks via a gas-tight syringe. Samples were injected into a CP-3800 gas chromatograph (GC) (Varian, Australia) equipped with a 2 m ⅛" Haysep R 60/80 mesh packed column for the separation of hydrocarbons; this was connected in series by time switching to a 2 m ⅛" Molsieve 5A 60/80 mesh packed column for the separation of permanent gases. Gases were detected using a two channel detector system combining a thermal conductivity detector and a flame ionisation detector. The electronic pressure control was set to 48 psi equating to a column flow of 100 ml min$^{-1}$. After injection into a 250 μl sample loop, $CO_2$ and C2-C6 hydrocarbons were separated on the Haysep R column. $H_2$, $O_2$/Ar, $N_2$, methane and carbon monoxide were not retained and passed directly onto the Molsieve column where they were trapped and isolated at 1.7 min. At 5.5 min the contents of the Molsieve column were put back in series with the Haysep R column together with the rest of the hydrocarbon gases. The temperature program had an initial temperature of 80° C. for 10 min followed by heating at 15° C. min$^{-1}$ to 200° C. (5 min hold). The GC was calibrated using a three point calibration using standard gas mixtures (BOC) with methane concentrations of 20.5 ppm, 2010 ppm, and 20000 ppm. Sample methane concentration was calculated from the FID channel responses using the Varian Star software (vers. 6.20).

For the Surat coal and formation water cultures (Examples 2 & 3), five ml gas samples were collected from septum sealed bottles via a gas-tight syringe. The composition of the culture gases were analysed using an Agilent Micro-GC model 490. Samples were injected into the front injection port of the GC by syringe pump. The Micro-GC is equipped with three different column modules: 10 m Molsieve 5 Å column with backflush, a 10 m Pora Plot Q column with backflush and a 10 m CP-Sil-50B column.

Gases were detected using a micro machined thermal conductivity detector for each module; limit of detection is in the order of ~1 ppm. The injector has a built-in 10 μl sample loop and the helium carrier pressure was set to 15 psi and the injector temperature was 90° C. The temperature of the Molsieve 5A column in channel 1, the Pora Plot Q column in channel 2 and the CP-Sil-5CB column in channel 3 was set to 90° C., 70° C. and 60° C., respectively. After being injected into Micro-GC, gases are drawn by a vacuum pump through the sample loop and then the inlet system injects the gas sample from the sample loop into the carrier gas stream. $O_2$/Ar, $N_2$, $CH_4$ and CO are separated on the Molsieve 5A column. $CO_2$, $C_2H_6$ and $C_3H_8$ are separated on the Pora Plot Q column. C4-C5 hydrocarbon gases and $H_2S$ are separated on the CP-Sil-5CB column.

Results and Discussion

Example 1. Effect of Addition of $NH_4Cl$ on Production of Methane with Yeast Extract as Carbon Source The methanogenic enrichment culture MBC3/4 derived from a coal seam formation water sample in Victoria was used to examine in particular, the effect of ammonium on the generation of methane from a complex organic substrate, yeast extract. In this experiment the P concentration was fixed at about 1752 μM and N was present in both the headspace gas (70 mL of 95% $N_2$ and in the yeast extract, typically about 10% N. Additional nitrogen was supplied to one of the conditions in the form of $NH_4Cl$ (~1.87 mM). The culture treatments were incubated at 30° C.

The headspace gas was analysed weekly for 6 weeks. The relative surface area of the carbonaceous material and the methanogenic enrichment culture to the volume of gas at the laboratory level was such to approximate the distribution of gas throughout a carbonaceous material upon injection of the gas into a coal seam.

Figure 1:
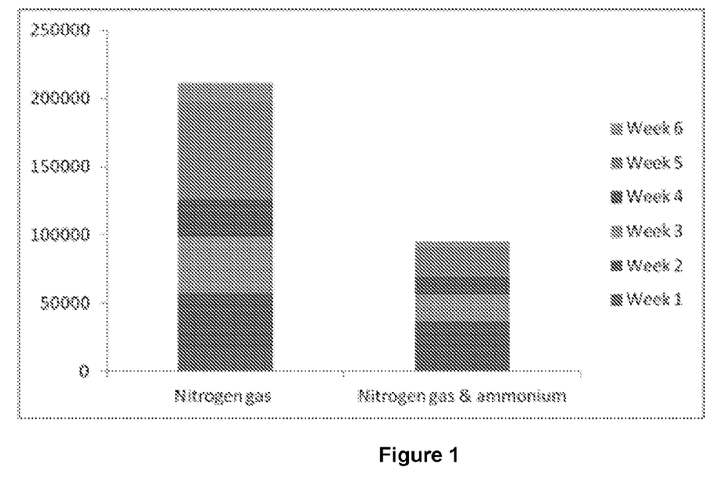
FIG. 1 is a bar graph representing methane concentration (ppm) in the headspace gas sampled on a weekly basis from yeast extract as a source of carbon using the MBC3/4 inoculum as described in the Example; and, FIG. 2 is another bar graph demonstrating the effect of nitrogen on methane concentration (%) in the headspace of vials containing Surat coal using the Surat methanogenic inoculums sampled after a 4 week period as described in the second Example; and, FIG. 3 is a graphical representation of methane concentration (mM) in the headspace of vials containing Surat coal using the Surat methanogenic inoculums sampled after a 4 week period as described in the third Example.

Data comprising methane concentration (ppm) in the headspace gas from yeast extract as a source of carbon using the MBC3/4 inoculum are presented as a stacked plot, with data from each week's measurements presented in a different colour. Nitrogen was supplied in the head space gas and in the yeast extract in both conditions. In the ammonium treatment, additional nitrogen was supplied as 1.87 mM $NH_4Cl$ (n=3).

Unexpectedly, the addition of $NH_4Cl$, a commonly used nitrogen source suppressed the production of methane compared to the control condition where the available nitrogen was present as nitrogen gas and a complex mixture of compounds present in the yeast extract (see FIG. 1). This was unexpected because ammonium ions are a readily assimilated form of N that are widely used by bacteria and archaea. The total amount of N in the form of ammonium ions in 50 ml of 1.87 mM is 93.5 micromoles. In comparison, 70 ml of headspace gas (95% $N_2$) and normal temperature and pressure would be 5.9 millimoles (of N atoms), however assuming that $N_2$ needs to be in solution to be available for use by the microflora, and the solubility of $N_2$ is about 0.017 g per kg of water (engineering toolbox.com) the concentration of $N_2$ in solution is 0.61 mM or 1.22 mM in terms of N atoms. Also present in both conditions was 500 mg/l yeast extract which is about 10% N by weight, thus contributing 178 micromoles of N at about 3.6 mM, principally in the form of protein. None the less, in this experiment the addition of $NH_4Cl$ to the medium actually decreased the yield of methane, despite the presence of a constant amount of $N_2$ in the headspace and protein in the medium.

Examples 2 and 3. Comparison of Nitrogen Sources on the Production of $CH_4$ Using Coal as the Source of Carbon This experiment used the Surat coal and water together with an inoculum derived from enrichment cultures of the Surat water which had been growing on coal for about 8 weeks. The temperature of the incubation was 42° C. The experiment was designed to focus on the conversion of coal (rather than yeast extract as in Example 1) to methane and to eliminate other sources of N.

Figure 2:
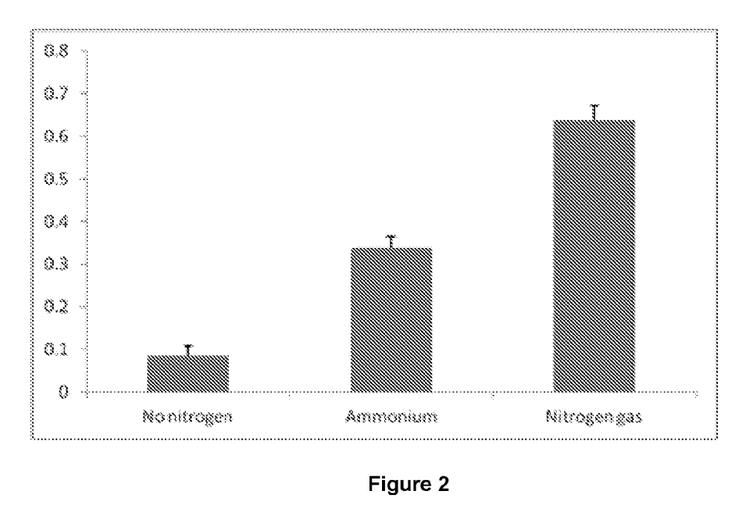
Figure 3:
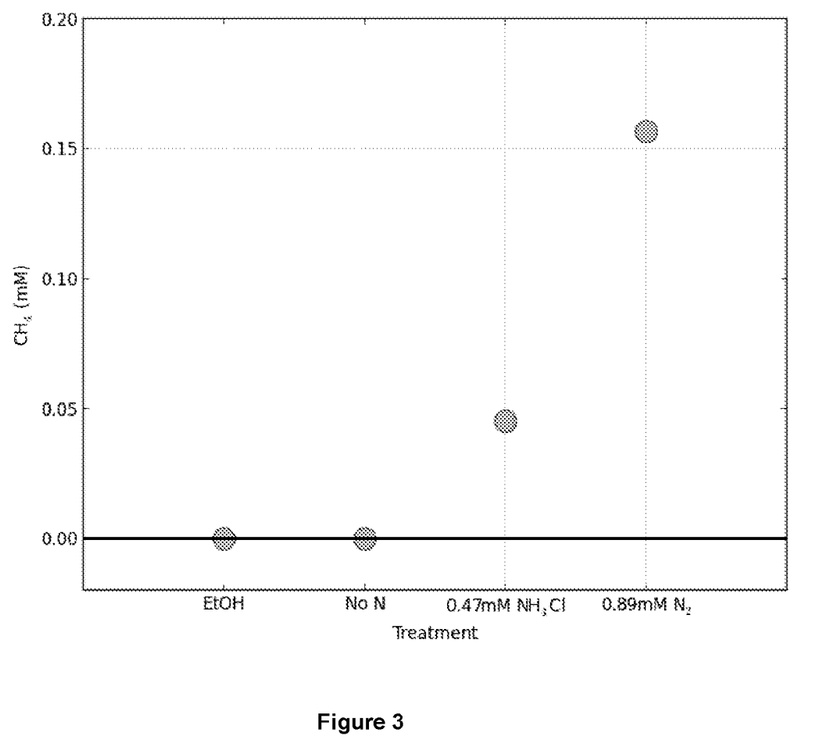

FIGS. 2 and 3 show the effect of nitrogen on methane concentration (%) in the headspace of the vials containing Surat coal using the Surat methanogenic inoculums after 4 weeks in culture. The results are derived from 5 replicates of the experiment of three treatments: the P concentration was fixed at 1.7 mM and no N other than that present in the coal was supplied, or N was supplied either as 1.9 mM $NH_4Cl$ in solution (Example 2) or 0.47 mM $NH_4CL$ in solution (Example 3), or N was supplied as 100 ml of 100% $N_2$ in the headspace gas. In the first two treatments, the headspace gas was initially 100% helium.

It is apparent from FIGS. 2 and 3, that $N_2$ in the headspace is more effective than the $NH_4^+$ ions in the medium.

The amount of $N_2$ dissolved in solution was estimated to be 20 mg/L.

This result is unexpected because higher yields of methane from coal are observed with a different (from Example 1) consortium of organisms when their N requirements are delivered via gaseous $N_2$ rather than $NH_4^+$ ions in solution. This is despite the considerable energetic cost that is required to reduce $N_2$ to $NH_3$.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Further, with regard to the various systems referred to throughout the specification, any system is to be understood as encompassing individual as well as plural structures that may or may not be physically connected.

REFERENCES

Li D, Hendry P, Faiz M. (2008) A survey of the microbial populations in some Australian coalbed methane reservoirs. *International Journal of Coal Geology*, 76, 14-24.

The invention claimed is:

1. A process for enhancing biogenic methane production from a carbonaceous material, the method comprising the steps of:
    dispersing a nutrient combination throughout the carbonaceous material for a period of time to biogenically produce methane, wherein the nutrient combination comprises a source of phosphorus (P) and gaseous nitrogen ($N_2$), and,
    collecting methane produced from the carbonaceous material,
    wherein the nutrient combination comprises:
    (i) an aqueous solution which comprises a phosphorus concentration of at least 1.5 mM; and
    (ii) dissolved gaseous nitrogen ($N_2$);
    wherein non-gaseous nitrogen represents no more than 50 wt % of the total nitrogen source in the nutrient combination; and wherein the nutrient combination is substantially free of sulphur containing oxides (SOx) and/or nitrogen containing oxides (NOx), and
    wherein the carbonaceous material is a carbon-containing substance capable of supporting one or more methanogenic microbial populations, and wherein the carbonaceous material is subject to degradation by the one or more methanogenic microbial populations to produce methane or methane precursors.

2. The process according to claim 1, wherein the carbonaceous material is an in situ carbonaceous material, and wherein dispersing said nutrient, combination throughout the carbonaceous material comprises: (i) injecting the nutrient combination into or proximal to the carbonaceous material, and/or (ii) co-injecting the nutrient combination with a hydraulic fracturing fluid, and/or (iii) dispersing a concentrated solution of the nutrient combination to the carbonaceous material, whereby the dispersed concentrated solution undergoes dilution with fluids associated with the carbonaceous material to provide a solution having an effective phosphorus concentration of at least 1.5 mM.

3. The process according to claim 1, wherein the carbonaceous material is an ex situ carbonaceous material in a heaped pile, and wherein dispersing said nutrient combination throughout the carbonaceous material comprises applying the solution of the nutrient combination to an outer surface of the heaped pile, under an atmosphere of gaseous nitrogen, in an amount sufficient to cause the solution to flow or trickle under gravity from the outer surface through underlying carbonaceous material in the heaped pile, optionally, wherein the gaseous nitrogen is applied to the heaped pile under positive pressure to ensure that the gaseous nitrogen penetrates and occupies any voids between the carbonaceous material in the heaped pile.

4. The process according to claim 1, wherein the carbonaceous material is an ex situ carbonaceous material in a reactor, and wherein dispersing said nutrient combination throughout the carbonaceous material comprises mixing the nutrient combination with the carbonaceous material in the reactor.

5. The process according to claim 4, wherein the mixing is continuous, intermittent, or ceases entirely after an initial mixing period, said period being sufficient to bring the nutrient combination into intimate contact with the carbonaceous material.

6. The process according to claim 1, wherein the gaseous nitrogen ($N_2$) comprises at least 60% v/v of the total gaseous component present in the nutrient combination.

7. The process according to claim 1, wherein the pH of the nutrient combination is equal to or greater than 7.

8. The process according to claim 1, wherein the nutrient combination comprises a two-phase mixture of a solution of a soluble source of phosphorus (P) and the gaseous nitrogen ($N_2$), or is in the firm of an emulsion.

9. The process according to claim 1, wherein the dissolved gaseous nitrogen ($N_2$) is at a concentration between 5 mg to 1750 mg of gaseous nitrogen per kilogram of a solvent.

10. The process according to claim 1, the nutrient combination further comprising a source of water, wherein the source of water comprises water, deionised water, ultrapure water, distilled water, municipal water, groundwater, produced water, formation water, recycled water, process water, wastewater, brackish water and/or brine.

11. The process according to claim 1, wherein the carbonaceous material is selected from the group consisting of coal, lignite, peat, drill cuttings, waste coal, coal derivatives, oil shale, oil formations, tar sands, hydrocarbon-contaminated soil, petroleum sludges, and combinations thereof.

12. The process according to claim 10, wherein the temperature, pH and/or ionic strength of the source of water is substantially the same as the temperature, pH and/or ionic strength of the nutrient combination.

13. The process according to claim 1, wherein the nutrient combination further comprises:
- at least one trace element selected from the group consisting of: iron, manganese, cobalt, zinc, molybdenum, nickel, aluminium, boron, copper, tungsten, selenium, and combinations thereof;
- at least one vitamin selected from the group consisting of: pyridoxine, aminobenzoic acid, pantothenate, nicotinic acid, riboflavin, thiamine, thioctic acid, biotin, folic acid, pyruvate, $B_{12}$, and combinations thereof;
- at least one additive selected from the group consisting of acids, bases, buffering agents, oxidants, anti-oxidants, surfactants, emulsifying agents, gelling agents, and combinations thereof;
- at least one stimulant selected from the group consisting of: yeast extract, Coenzyme, M, lactic acid, minerals, alkyl alcohols, vanillate, glycine, cysteine, 3,4,5-trimethoxybenzoate, cellulose, cinnamic acid, benzoic acid, chitin, chitosan, chlorate, perchlorate, and combinations thereof; and/or
- one or more methanogenic microbial populations, containing one or more methanogenic microbes selected from the group consisting of: Methanobacteria, Methanococci, Methanomicrobia, and Methanopyri.

14. A process for enhancing biogenic methane production from a carbonaceous material, the method comprising the step of:
dispersing a nutrient combination to the carbonaceous material for a period of time to biogenically produce, methane, wherein the nutrient combination comprises phosphorus (P) and gaseous nitrogen ($N_2$), wherein the nutrient combination is substantially free of oxygen, and/or is substantially free of sulphur-containing oxide ($SO_x$) and/or nitrogen-containing oxides ($NO_x$), and wherein the carbonaceous material is a coal deposit, coal, lignite, peat, waste coal, a coal derivative, or a combination thereof.

15. The process of claim 14, wherein the nutrient combination comprises a two-phase mixture of a solution of phosphorus (P) and the gaseous nitrogen ($N_2$).

16. The process of claim 15, wherein the solution comprises phosphorus at a concentration of at least 1.5 mM.

17. The process of claim 14, wherein the nutrient combination is in the form of an emulsion.

18. The process of claim 14, wherein the nutrient composition further comprises one or more methanogenic microbial populations, wherein the methanogenic microbial populations comprise one or more methanogenic microbes selected from the group consisting of Methanobacteria, Methanococci, Methanomicrobia, Methanopyri, and combinations thereof.

* * * * *